(12) United States Patent
Henry (10) Patent No.: US 7,398,880 B2
(45) Date of Patent: Jul. 15, 2008

(54) SCALPEL BLADE REMOVER

(75) Inventor: Robert Anthony Neville Henry, Queensland (AU)

(73) Assignee: Qlicksmart Pty. Ltd., West End, Queensland (AU)

( * ) Notice: Subject to any disclaimer, the term of this patent is extended or adjusted under 35 U.S.C. 154(b) by 415 days.

(21) Appl. No.: 11/255,266

(22) Filed: Oct. 21, 2005

(65) Prior Publication Data

US 2006/0041267 A1    Feb. 23, 2006

Related U.S. Application Data

(63) Continuation of application No. PCT/AU2004/000533, filed on Apr. 23, 2004.

(30) Foreign Application Priority Data

Apr. 24, 2003    (AU) .............................. 2003901949

(51) Int. Cl.
*B65D 83/10*    (2006.01)
*A61B 17/3217*    (2006.01)

(52) U.S. Cl. ...................... 206/355; 206/359; 206/363; 29/239

(58) Field of Classification Search ................ 206/354, 206/355, 359, 363–366, 370, 438, 564, 565; 29/239, 270, 278, 426.5; 606/167; 604/110
See application file for complete search history.

(56) References Cited

U.S. PATENT DOCUMENTS

| | | | |
|---|---|---|---|
| 4,746,016 A | | 5/1988 | Pollak et al. |
| 4,998,334 A | * | 3/1991 | Pemberton et al. ............ 29/239 |
| 5,088,173 A | | 2/1992 | Kromer et al. |
| 5,361,902 A | | 11/1994 | Abidin et al. |
| 5,667,067 A | * | 9/1997 | Gabriel ........................ 206/355 |
| 5,699,908 A | * | 12/1997 | Frye et al. .................... 206/355 |
| 5,938,027 A | | 8/1999 | Soroff et al. |
| 6,216,868 B1 | * | 4/2001 | Rastegar et al. ............. 206/359 |

\* cited by examiner

*Primary Examiner*—Mickey Yu
*Assistant Examiner*—Melissa L Lalli
(74) *Attorney, Agent, or Firm*—Panitch Schwarze Belisario & Nadel LLP (57) ABSTRACT

A single-use scalpel blade remover (1) removes a blade (33) from a tang (32) of a scalpel (30) and captures it, in a single-handed operation. The remover (1) comprises a housing (2) having a detent (16), and an actuator (3) which is operatively juxtaposed with the housing (2) and moveable alongside the housing in a forward direction from a proximal position (whereat an opening is formed between the proximal ends of the actuator and the housing) to a distal position (whereat the detent (16) engages the proximal end of the actuator). The blade remover (1) also includes a cam-operated mechanism (14,23,20) for automatically separating the heel of the blade (33) from the tang (32) as the actuator (3) is moved to the distal position. In use, the blade (33) on the tang (32) is inserted in the opening and the actuator is pushed forward by the tang to its distal position, whereupon the detent (16) engages the proximal end of the actuator (3) and retains it in its distal position and prevents rearward movement of the blade (33). As the heel has been separated from the tang (32), upon withdrawal of the tang from the scalpel blade remover (1), the blade (33) is stripped from the tang and retained captively between the actuator (3) and the housing (2).

25 Claims, 9 Drawing Sheets

SCALPEL BLADE REMOVER

CROSS-REFERENCE TO RELATED APPLICATION

This application is a Continuation of International Application No. PCT/AU2004/000533, filed Apr. 23, 2004, which was published in the English language on Nov. 4, 2004, under International Publication No. WO 2004/093706 A1 and the disclosure of which is incorporated herein by reference.

The present invention relates to a scalpel blade remover. In particular, the present invention relates to a scalpel blade remover that enables a blade to be removed from a scalpel and retained in the remover.

BACKGROUND ART

A conventional surgical scalpel typically comprises a reusable, sterilisable elongate handle or haft onto which a replaceable slotted blade is mounted. At the distal end of the handle is a tang that normally includes opposed grooves or channels to receive the blade. Generally the tang is a narrow extension of the handle. The blade has a slot extending longitudinally, which slot has a portion of sufficient width to be received over the tang and a narrower portion at its distal end whereby the edges of the slot are closely received in the opposed grooves. The blade may have a heel that is received in a recess in the handle. The term "heel" is intended to refer to the proximal portion of the blade, i.e. the end portion nearer the user's hand.

The handle is intended to be used repeatedly, but the blade is normally discarded after single use, or if the blade becomes dull or contaminated, or if a different style of blade is required. In many operations several blades are required and are typically used successively on the same handle. In order to remove the blade from the handle, the heel portion of the slotted blade must be bent out of its plane (i.e. separated or lifted off the handle), and then the blade may be moved axially along the tang so that the heel portion rides over the tang thereby releasing the tang from the slot.

Manual removal of the blade can be hazardous. During the manipulation of the blade the operator is put at risk of being cut on the sharp blade. With the ever-increasing spread of blood transmitted diseases such as AIDS and hepatitis, any accidental injury from the blade can result in infection or contamination.

Many forms of mechanical scalpel blade removers are known. Most of these require two-handed operation, or bending or twisting of the scalpel, rendering them dangerous and/or awkward to use.

U.S. Pat. No. 5,699,908 describes a cam-operated device for removing the blade from the handle of a scalpel. Our earlier invention is described in U.S. Pat. No. 5,875,533. The devices described in both U.S. Pat. No. 5,699,908 and U.S. Pat. No. 5,875,533 are advantageous as they permit a blade to be removed from the scalpel by moving the scalpel in and out of the device in a substantially linear path, in a single-handed operation. Each such scalpel blade remover allows successive scalpel blades to be removed and stored within a sharps container associated it. The devices described in U.S. Pat. No. 5,699,908 and U.S. Pat. No. 5,875,533 are specifically designed for repeated use, and the withdrawal of the scalpel handle resets the device for further use.

As mentioned above, many blades may be used in a surgical procedure and theatre protocol requires that all items used during a surgical procedure be accounted for. As the devices of U.S. Pat. No. 5,699,908 and U.S. Pat. No. 5,875,533 are designed for repeated use, and since they store multiple blades within a single container, they render it difficult to account accurately for all blades used during a surgical procedure. Furthermore an operating theatre is a sterile environment and prior to such a scalpel blade remover being introduced to a theatre, it must be sterilised. This is not readily possible with multiple blades being stored within a sharps container unless the container is emptied prior to each sterilisation.

It is an object of the present invention to provide a scalpel blade remover that overcomes or ameliorates one or more of the disadvantages described above, or which at least provides the consumer with a useful choice.

SUMMARY OF THE INVENTION

In one form, the present invention provides a scalpel blade remover for removing a blade having a heel from a tang of a scalpel, the remover comprising:

a housing;

an actuator having a proximal end, the actuator being operatively juxtaposed with the housing and moveable relative to the housing from a proximal position whereat an opening is formed between the actuator and the housing for receiving therebetween the blade on the tang of the scalpel, to a distal position;

a blade deflecting mechanism for automatically separating the heel of the blade from the tang of the scalpel as the actuator is moved to the distal position; and a retention mechanism for engaging the actuator and retaining it in the distal position;

wherein in use, when the blade on the tang is inserted in the opening and the actuator is pushed forward by the tang to its distal position, the blade deflecting mechanism automatically separates the heel of the blade from the tang of the scalpel, the retention mechanism engages the actuator and retains it in its distal position and limits rearward movement of the blade, and upon withdrawal of the tang from the scalpel blade remover, the blade is stripped from the tang and retained between the actuator and the housing.

The scalpel blade remover of this invention has the advantages of those described in U.S. Pat. No. 5,699,908 and U.S. Pat. No. 5,875,533, namely the blade can be removed safely and automatically by moving the scalpel handle single-handedly in a simple in-out movement along a linear path. However, unlike the prior art scalpel blade removers, the scalpel blade remover of this invention is single use only, and the removed blade is encapsulated between the housing and actuator. The scalpel blade remover of this invention can therefore be used in sterile environments, and facilitates the counting of used blades.

In one embodiment, the retention mechanism engages the proximal end of the actuator and remains engaged with that end to thereby retain the actuator in its distal position and limit rearward movement of the blade.

Preferably, the housing has a resiliently flexible arm which is deflected as the actuator is pushed towards its distal position by the tang of the scalpel. The retention mechanism can be a detent formation on that arm. When the actuator reaches its distal position, the arm springs back and the detent formation engages the proximal end of the actuator with an audible "click". This click indicates to the user that the detent formation has engaged the actuator, and the scalpel handle can be withdrawn to strip the blade from the tang.

The detent formation prevents the movement of either the actuator or the blade in the reverse direction. With the actuator retained in the distal position, the scalpel blade remover cannot subsequently be used to remove other blades. In such condition, the scalpel blade remover may be used to readily account for blades used in a surgical procedure. The removed blade is retained within the scalpel blade remover where it is not a sharps risk.

The detent formation may suitably comprise two spaced sawtooth detents on either side of the opening. The blade of the scalpel may be operatively inserted through the opening between the actuator and the housing in a linear path. On further insertion of the blade, the handle of the scalpel engages the actuator and pushes it towards the distal position. Typically the actuator is engaged by a shoulder adjacent the tang, although the tang itself or other portions of the handle may be brought into engagement with the actuator. As the actuator is pushed in a longitudinal direction towards the distal end of the housing, the blade deflecting mechanism automatically separates the heel of the blade from the tang of the scalpel.

Other suitable mechanisms may be used to lock the actuator in the distal position, such as a ratchet mechanism, a key mechanism, a catch mechanism, or the like. The retention mechanism may engage the actuator at a location thereon other than its proximal end Typically, the blade deflecting mechanism is cam operated. In a preferred embodiment, the blade deflecting mechanism comprises a cam surface on the housing; and a cam follower on the actuator adjacent its proximal end. In use, the cam follower engages with the cam surface as the actuator is moved to the distal position to cause the proximal end of the actuator to disengage the heel of the blade from the tang.

The housing and the actuator may be two separate pieces. Advantageously however, the housing and the actuator are integrally formed, and a bi-fold portion is connected between the distal end of the actuator and the distal end of the housing. The scalpel blade remover may be manufactured of thermoplastics material by injection moulding. For example, the scalpel blade remover may be conveniently injection moulded from a thermopolymer such as polypropylene or polyethylene.

The housing is typically of channel section with opposed sidewalls and a web or base portion. The actuator is operatively located within the housing in a snap fit and can be retained therein by tabs on the sidewalls. These tabs also serve to guide the movement of the actuator within the housing. The resiliently flexible arm may be a cantilevered portion of the base.

The base of the housing may cooperate with the actuator to clasp the distal end of the blade. The distal end of the actuator may be deflected towards the base as it moves to its distal position. The resistance of the resiliently flexible arm to deflection by the actuator clasps the blade therebetween. The resiliently flexible arm may be stiffened with longitudinal reinforcing ribs.

The opposed longitudinal sidewalls may each be formed with a cam surface projecting from the inner face of the sidewalls. Alternatively the cam surface may be provided as a groove or channel in or extending through the sidewalls. In a preferred configuration the sidewalls may each be formed with a thickened section wherein the ridge of the thickened section acts as the cam surface. Preferably the cam surface is an arcuate or inclined surface that urges the cam follower to be deflected transversely in response to longitudinal movement relative to the housing.

The proximal end of the actuator may suitably be bifurcated, with a longitudinal slot for receiving the tang, and a pair of legs having guide surfaces for engagement with the blade on opposite sides of the tang. A cam follower is preferably disposed on each of the legs of the bifurcated proximal portion of the actuator, for engagement with a cam surface on a respective sidewall.

A stop may be provided at the distal end of each cam surface to prevent the actuator from moving beyond the distal position. The stop may preferably be in the form of a step in the cam surface.

The housing may also include an end wall. The end wall may serve to protect the operator from forcing the blade of the scalpel too far into the scalpel blade remover whereby it unintentionally extends beyond the housing resulting in increased risk of a sharps injury. The end wall may also serve to brace the sidewalls in the desired position.

The scalpel blade remover can be formed from a translucent or transparent material to allow convenient visibility of the captured blade for positive accounting and confirmation that the device contains a removed blade. It is further preferred that the actuator and the housing be visually distinguishable from each other, such as by the use of materials having differing colours and/or textures, or by application of a paint to at least one of them. This will assist the user in correctly inserting the blade into the device. The blade is then simply inserted between the two distinct components for correct functioning of the blade remover. The scalpel blade remover of the present invention may also include means for instructing a user as to the correct blade orientation to prevent upside down insertion of the scalpel into the scalpel blade remover. The scalpel blade remover preferably allows a user to remove and re-orientate a scalpel in the event of an upside down insertion.

It is also preferred that actuator and housing be substantially spaced apart in their ready state to provide a visually distinct entry for the blade, and to reduce the precision required in positioning the blade for insertion.

The scalpel blade remover of the present invention may readily be sterilised by gamma-radiation or other convenient means. A preferred form of sterilisation is to permeate a sealed package containing a scalpel blade remover with ethylene oxide.

The housing may further include a support or brace between the front ends of the sidewalls, to assist in retaining the sidewalls in position. The support or brace may also serve to guide the scalpel into the opening between the housing and the actuator.

Advantageously, the scalpel blade remover of the present invention permits a variety of blade types and shapes to be removed from a large number of handle sizes and makes. In a preferred configuration, the scalpel blade remover of the present invention resists the partial removal of a scalpel blade and subsequent jamming. Thus, the scalpel blade remover is less likely to be rendered inoperable as a result of a jammed blade. The scalpel blade remover of the present invention retains the scalpel blade in the housing whereby its subsequent use is prevented. Thus, the number of blades may be readily accounted for by simply counting the number of used scalpel blade removers having a blade therein. As described above, the scalpel blade removers may allow the scalpel blade to be seen through the materials of construction of the housing.

A plurality of scalpel blade removers of the present invention may be retained within recesses in a holder or sharps container. The holder or sharps container may be adapted to be hand-held for left or right handed use, or may include means for securely mounting the container to a support surface. Advantageously, a large number of scalpel blade devices may be stacked to form a block in the holder that may be considered as a sharps container where each blade is retained in a separate housing. A holder having a stack of scalpel blade removers may be configured such that the removers are retained in the stack or may be removed from the stack once each scalpel blade remover has been used.

In another form, the invention provides a method of removing a blade from a tang of a scalpel using a scalpel blade remover having a first member, a second member juxtaposed with the first member, the first and second members defining a narrow space therebetween for receiving the blade on the tang, said second member being moveable relative to the first member from the first position to a second position, a blade deflector for separating the heel of the blade from the tang of the scalpel as the second member is moved to the second position, and a mechanism for retaining the second member in the second position;

the method comprising the steps of:

inserting the blade between the first and second members with the blade mounted on the tang of the scalpel;

engaging the second member with the scalpel;

applying a force on the scalpel sufficient to move the second member relative to the first member from the first position to the second position, and to cause the blade deflector to separate a heel of the blade from the tang;

causing the mechanism to retain the second member in the second position; and withdrawing the scalpel to strip the blade from the tang and leave it retained between the first and second members.

Preferably, the step of applying a force includes causing a cam follower on the second member to move along a camming surface of the first member as the second member is moved to the second position. The blade deflector is urged by the cam follower into engagement with the heel of the blade to separate the heel from the tang as the second member moves to its second position, and holds the heel off the tang when the second member is retained at the second position.

Typically, the step of causing the mechanism to retain the second member in the second position includes engaging the second member with a detent.

In order that the invention may be more fully understood and put into practice, preferred embodiments thereof will now be described by way of example only, with reference to the accompanying drawings.

DESCRIPTION OF PREFERRED EMBODIMENTS

Figure 1:
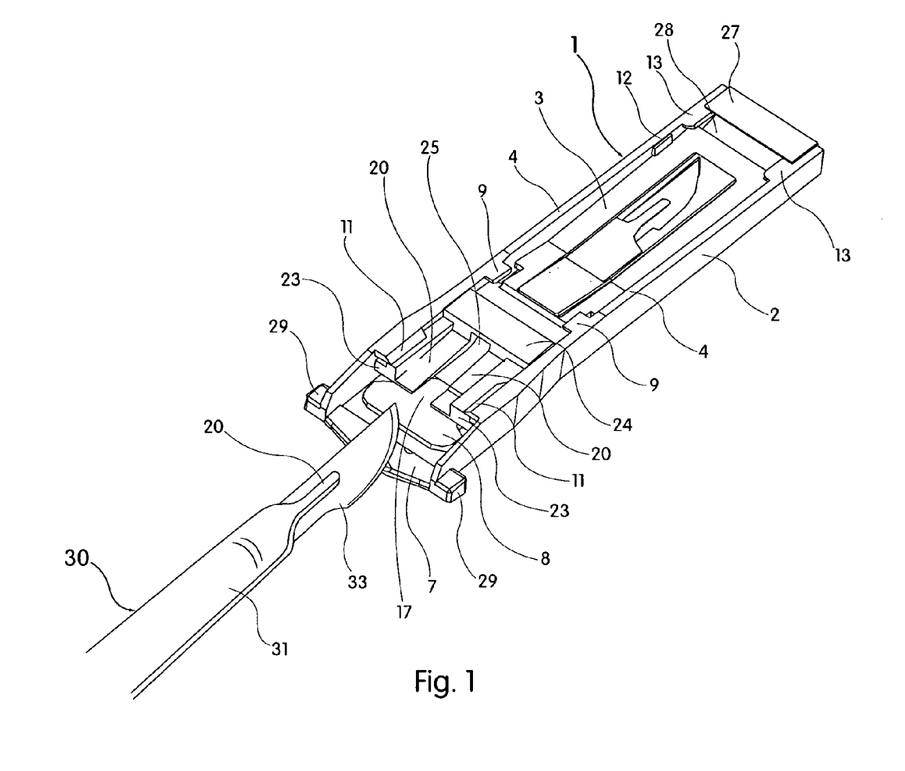
FIG. 1 is a perspective view of a scalpel blade remover according to one embodiment of the present invention, ready for use.

FIG. 1 shows a scalpel blade remover 1 comprising two main parts, namely a housing 2 and an actuator 3. In use, the actuator 3 is disposed within the housing 2. The scalpel blade remover 1 will be described with reference to its horizontal orientation as shown in the drawings. However, the blade remover can be used vertically or in any other suitable orientation, and the interpretation of the terms such as "upper", "lower", "above" and "below" as used herein is to be varied accordingly.

Figures 2, 3:
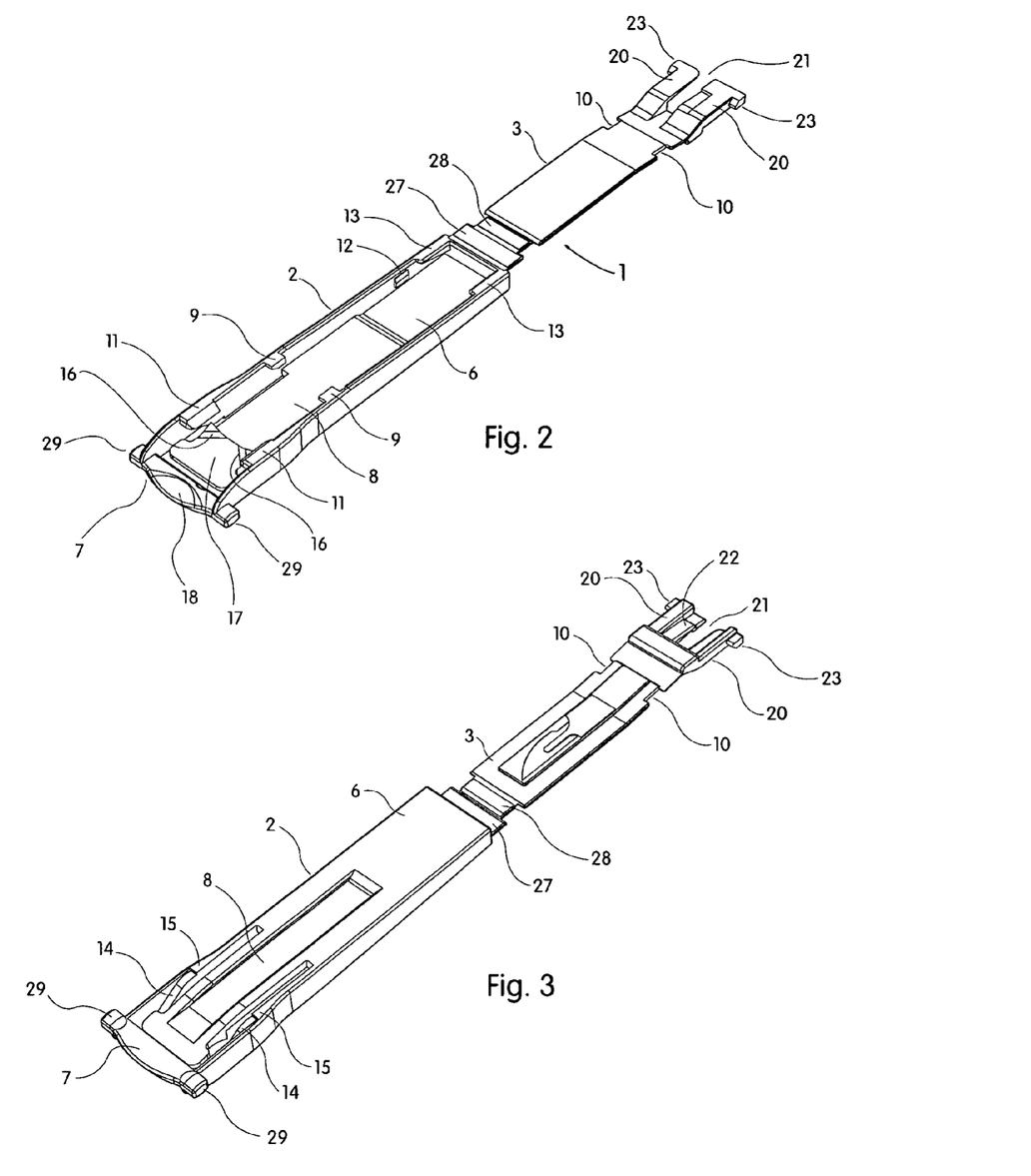
FIG. 2 is a perspective view from above of the scalpel blade remover of FIG. 1, shown open.
FIG. 3 is a perspective view from below of the scalpel blade remover of FIG. 1, shown open.

The housing 2 has two opposed sidewalls 4, an end wall 5 at one end (hereafter referred to as the "distal end"), a base 6 spanning between the side walls for part of their length from the end wall, and a bridge or brace 7 which is co-planar with the base and extends between the sidewalls 4 at the other end (hereafter referred to as the "proximal end"). The base 6 has a cantilevered portion which extends towards the brace 7 and forms a leaf spring 8.

Inwardly extending retaining lugs 9 are provided on the sidewalls 4 intermediate their ends. Corresponding cut-outs or slots 10 are provided in the longitudinal edges of the actuator 3 to permit the actuator to pass between the lugs 9 and nest within the sidewalls 4.

A first pair of pawl-like retaining lugs 11 are provided near the upper edge of respective opposite sidewalls 4 in the proximal region of the housing. A second pair of pawl-like retaining lugs 12 are provided at about mid-height on respective opposite sidewalls 4 near the distal end. The inwardly-extending lugs 11,12 have tapered inside faces and form ratchet-like sawtooth detents. The housing 2 and actuator 3 are made of stiff, but resiliently flexible plastics material. The flexibility of the sidewalls 4 permits the actuator 3 to be press fit between the opposed pairs of retaining lugs 11,12, whereupon the lugs 11,12 retain the actuator 3 within the housing 2.

Flanges 13 extend inwardly from the upper edges of the sidewalls 4 adjacent their junction with the end wall 5. Each flange 13 serves as a retaining lug and has a downwardly tapering cam surface under it.

The sidewalls 4 each have a downwardly facing cam surface 14 thereon, each cam surface 14 terminating in a stop 15.

The leaf spring has a detent formation in the form of a pair of catches or detents 16 in the region of its free end. These detents are of sawtooth longitudinal section, with abrupt faces on their distal side and slopes on their proximal sides. The detents 16 also have a scalloped portion 17 between them, and the brace 7 is provided with a chamfered or scalloped landing pad 18, to guide a scalpel into the slot formed between the housing 2 and the actuator 3 as described below.

The proximal end of the actuator 3 is bifurcated into two legs 20 on opposite sides of a slot 21 dimensioned to receive the tang of a scalpel handle. Each leg 20 has an inner guide portion with a tapered edge at its proximal end, and an outer guide rail 22 thereon. The actuator 3 is provided with a pair of cam followers 23, each positioned on the outside of a respective leg 20 of the actuator 3 at the proximal end thereof. The actuator also has a transverse bridge 24 at the distal ends of the legs 20. The bridge 24 has a tunnel 25 therein dimensioned to receive the tang of the scalpel handle.

Preferably, the scalpel blade remover 1 is integrally formed as a single piece by injection moulding, with the actuator 3 and housing 2 joined by an articulated connection, such as a bi-fold join. The bi-fold join is formed by a flap 27 hingedly connected to the end wall, and a neck portion 28 hingedly connected to the actuator 3, the flap 27 and neck portion 28 being connected but pivotable relative to each other about a transverse axis at their connection. The neck portion 28 is of reduced width and dimensioned to fit between the flanges 13.

Figure 4:
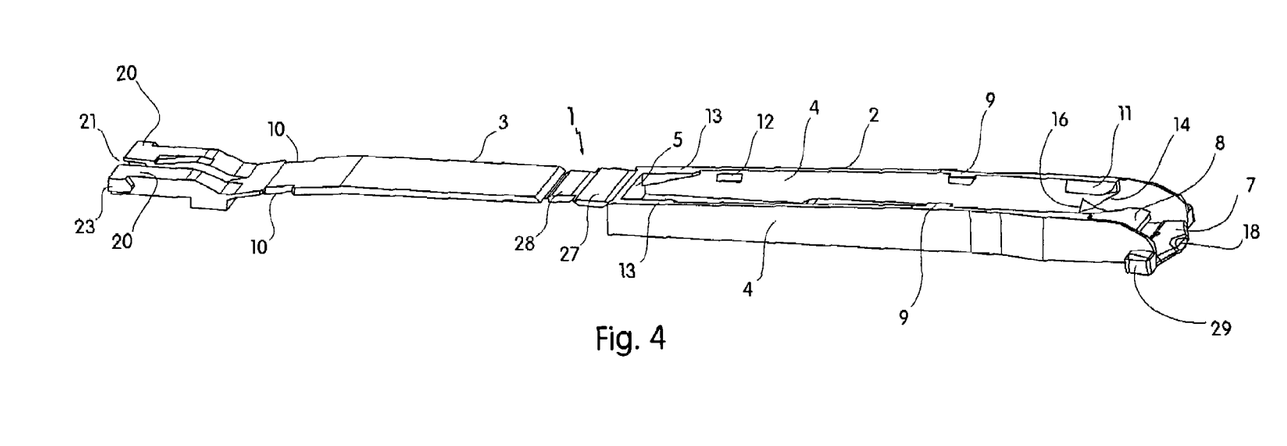
FIG. 4 is a perspective view from the side of the scalpel blade remover of FIG. 1, shown open.
Figure 5:
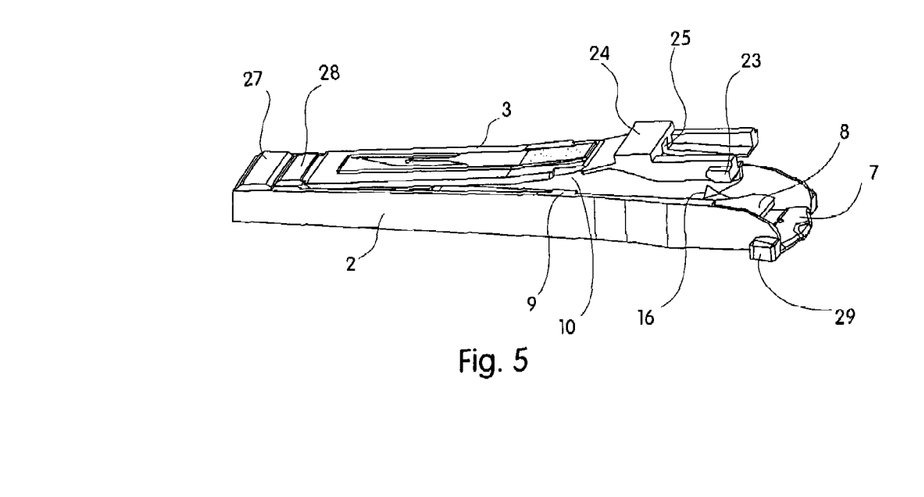
FIG. 5 is a perspective view from the side of the scalpel blade remover of FIG. 1, shown partially closed.

When manufactured as a single piece by injection moulding, the scalpel blade remover is normally in an open configuration as shown in FIG. 4. It is configured for use by first folding the actuator 3 until the flap 27 rests on the flanges 13 as shown in FIG. 5. The neck portion 28 is then folded at the fold lines at its ends to pass between the flanges 13, and the actuator is pressed into the housing 2. The slots 10 are aligned with the lugs 9 to permit the actuator to be received within the housing. The actuator 3 is snap fitted past the retaining lugs 11, 12 which then retain the actuator within the housing, ready for use, as shown in FIG. 1. It is to be noted that on assembly, the actuator is in a proximal position, i.e. nearer to the brace 7. Due to the bi-fold connection of the neck portion 28, the actuator is able to move longitudinally within the housing to a distal position, i.e. further from the brace.

On assembly, the high points of the detents 16 on the leaf spring 8 abut the actuator 3 and bias it to its rest position against the lugs 11. The detents 16 also space the leaf spring 8 from the actuator 3, and create a visible opening or mouth for the insertion of a scalpel blade. The actuator may have a marking or other sign thereon showing the correct orientation of the scalpel handle for entry into the opening, as depicted in FIG. 1. This sign may be moulded into the actuator at manufacture.

Figure 6A:
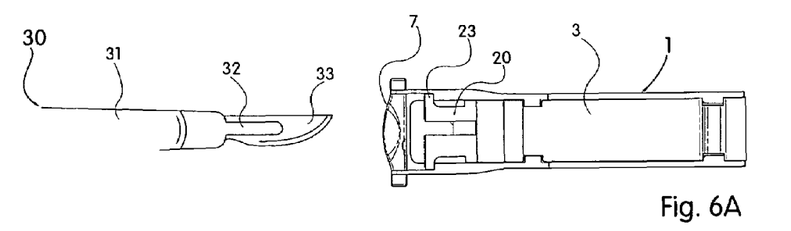
FIGS. 6A to 6G are sectional side views of the scalpel blade remover of FIG. 1 illustrating its operation.
Figure 6B:
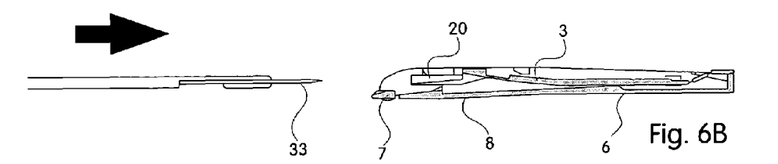

The operation of the scalpel blade remover 1 is illustrated in FIGS. 6A to 6G. FIG. 6A is a top view of the scalpel blade remover 1 ready for use. A scalpel 30 is about to be inserted into the scalpel blade remover 1. The scalpel 30 includes a handle 31 with a tang 32 at the distal end thereof. A scalpel blade 33 is shown attached to the tang 32. FIG. 6B shows the scalpel blade remover 1 in cross section.

Figure 6C:
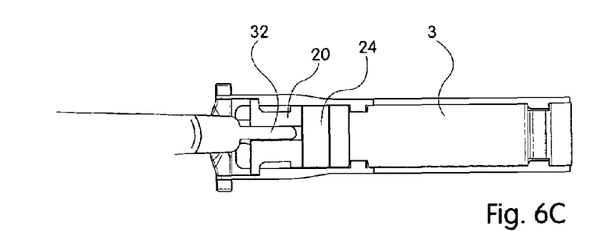
Figure 6D:
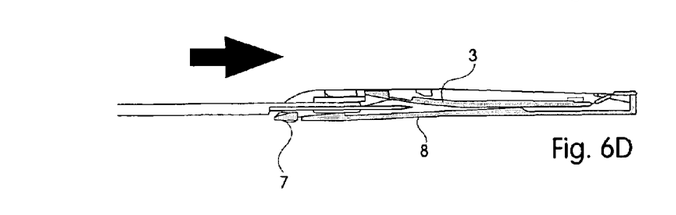

FIG. 6C is a plan view of the scalpel 30 engaging the scalpel blade remover 1, and FIG. 6D is a cross section of FIG. 6C. The scalpel is inserted into the scalpel blade remover 1 in a substantially linear path. The distal end of the scalpel (blade side down) is passed over the brace 7 and received in the "mouth" formed by the opening between the housing 2 and the actuator 3. The tang 33 is received in the slot 21 between the legs 20, while the blade passes under the guide portions of the legs 20.

Figure 6E:
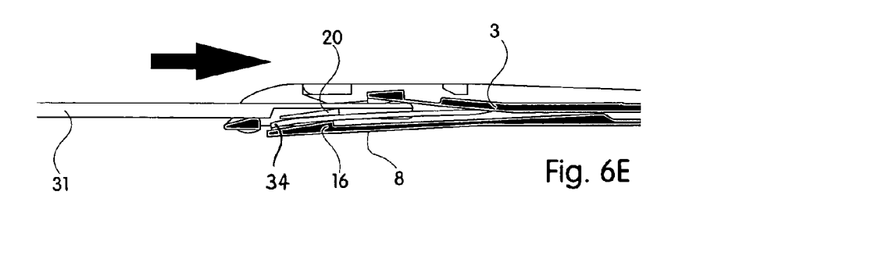

As the scalpel 30 is pushed into the scalpel blade remover 1, the tang passes into the tunnel 25 below the bridge 24 (as shown in FIG. 6E), and begins to deflect the leaf spring 8 downwardly. The blade is slightly arched as the leading portion of the blade is deflected downwardly by the actuator (held down by the lugs 12). When the heel of the blade clears the brace 7, the guide portions of the actuator legs 20 begin to deflect the heel 34 of the blade 33 downwardly off the tang.

Figure 6F:
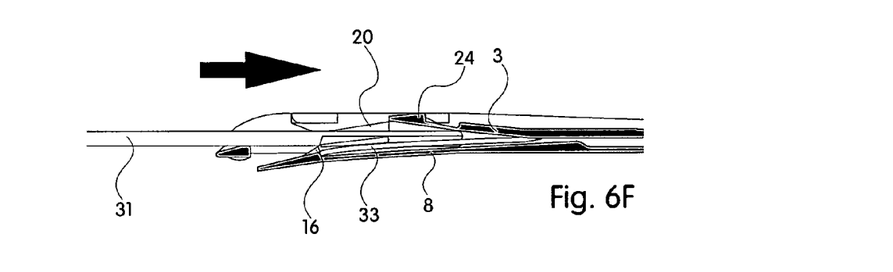

As the scalpel is pushed further into the scalpel blade remover, the handle abuts against the bridge 24 and pushes the actuator longitudinally along the housing 2 towards a distal position, shown in FIG. 6F. This causes the cam followers 23 on the actuator legs 20 to follow the respective cam surfaces 14, deflecting the legs 20 downwardly and positively lifting the heel of the blade 33 off the tang 32. As it moves forward, the actuator rides over the detents 16, bending the leaf spring 8.

The forward longitudinal motion of the actuator 3 is limited by its cam followers 23 reaching the cam stops 15. However, shortly before this limit is reached, the free ends of the actuator legs 20 clear the detents 16 on the flexed leaf spring 8, permitting the leaf spring and detents to snap back behind the blade and the actuator legs 20 with an audible "click" sound. The detents 16 engage and hold the actuator 3 in its distal position. The blade is sandwiched between the actuator 3 and the housing 2, with the heel of the blade separated from the scalpel tang. The click sound serves as a signal to the user that the blade has been captured and the handle can be withdrawn form the scalpel blade remover.

Figure 6G:
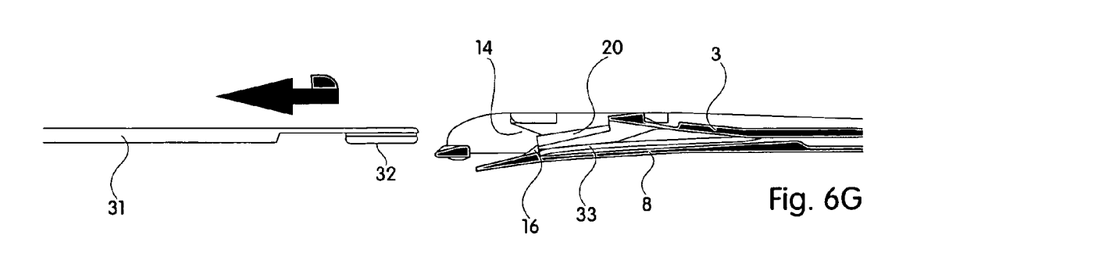

FIG. 6G shows the handle 31 of the scalpel 30 being withdrawn from the scalpel blade remover 1. Since rearward motion of the blade is prevented by the detents 16, and the heel of the blade is separated from the tang, the blade is stripped from the tang as the handle is withdrawn, leaving the blade securely held between the engaged actuator 3 and housing 2.

The detents 16 prevent the actuator returning to its start position, and hence prevent the device being re-used. The illustrated scalpel blade remover is a single use device which retains a single blade, enabling such blades to be easily accounted for. Moreover, the scalpel blade remover can be provided in a sterile envelope or packet for use in theatre. The scalpel blade remover also has the advantages of safe operation, economy of manufacture and ease of use.

Figure 7:
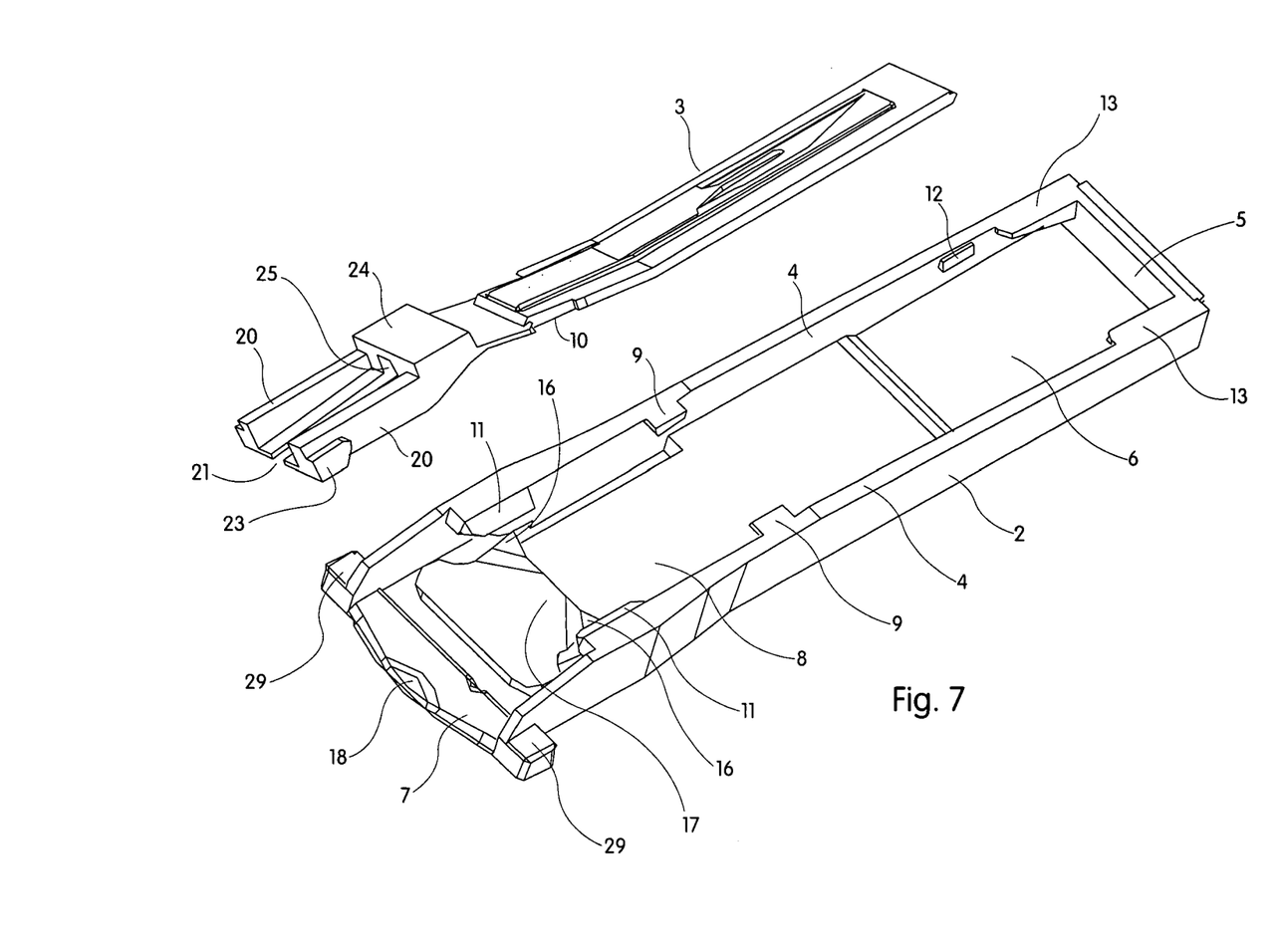
FIG. 7 is an exploded perspective view of a scalpel blade remover according to another embodiment of the present invention.

In another embodiment of the invention, shown in FIG. 7, the housing 2 and actuator 3 are formed as two separate parts. This embodiment is generally similar to that of FIGS. 1-4, but with the omission of the bifold hinge. The same reference numerals have been used in FIG. 7 for corresponding parts of the embodiments of FIGS. 1-4 and FIG. 7. The scalpel blade remover of FIG. 7 can be used in the same manner as the scalpel blade remover of FIGS. 1-4.

Figure 8:
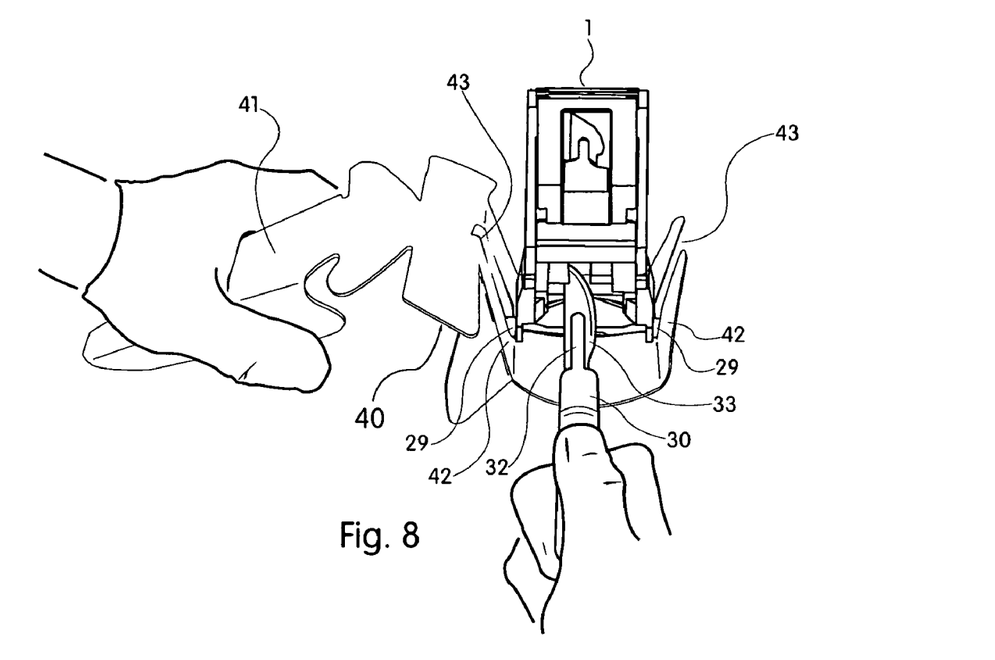
FIG. 8 is a perspective view of a scalpel blade remover of the present invention mounted in a handheld holder for right hand operation.

The scalpel blade remover of this invention may be mounted in a handheld holder 40 as shown in FIG. 8. The holder 40 is made from a suitable material, such as folded lightweight sheet metal, or rigid plastics material. The holder includes a handle 41 for the operator to grip. The handle 41 maintains the user's hand at a safe distance from the scalpel, and is bent downwardly so that the hand is shielded. The holder 40 has a channel portion with splayed walls 42. Each wall 42 has a vertical slot 43. The scalpel blade remover 1 is provided with a pair of mounting lugs 29 on opposite ends of the brace 7. The scalpel blade remover 1 is mounted in the holder 40 by sliding the mounting lugs 29 down into respective slots 43, to sit in the bottom of the channel. The scalpel blade remover 1 is thereby retained securely and safely in the holder. After use, the scalpel blade remover can simply be removed from the holder by lifting the mounting lugs 29 out of the slots 43.

Figure 9:
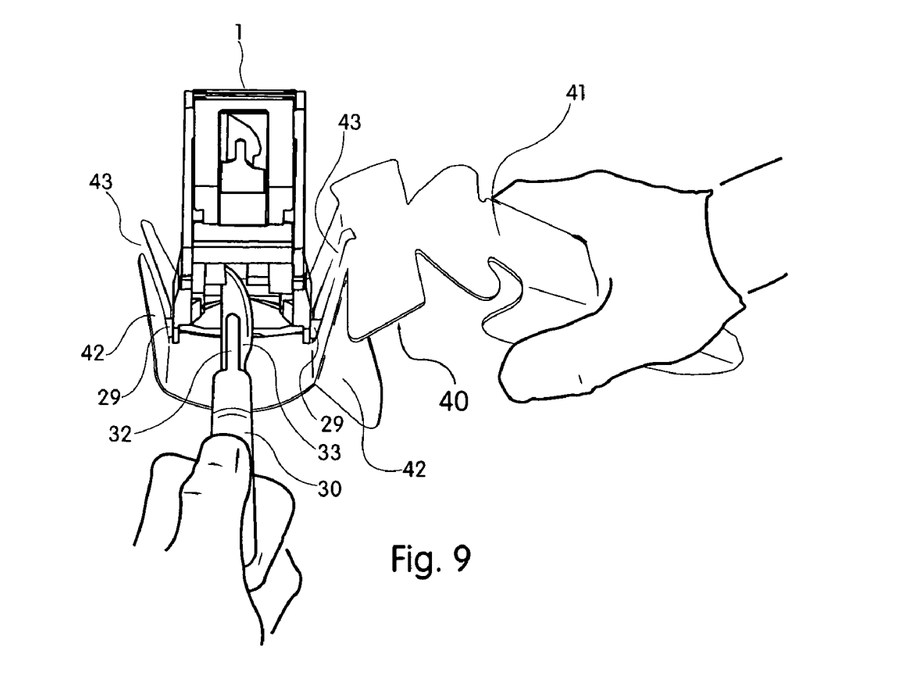
FIG. 9 is a perspective view of a scalpel blade remover of the present invention mounted in a handheld holder for left hand operation.

The scalpel blade remover is reversibly mountable in the holder 40, allowing it to be used for left and right handed operations as shown in FIGS. 8 and 9.

Figure 10:
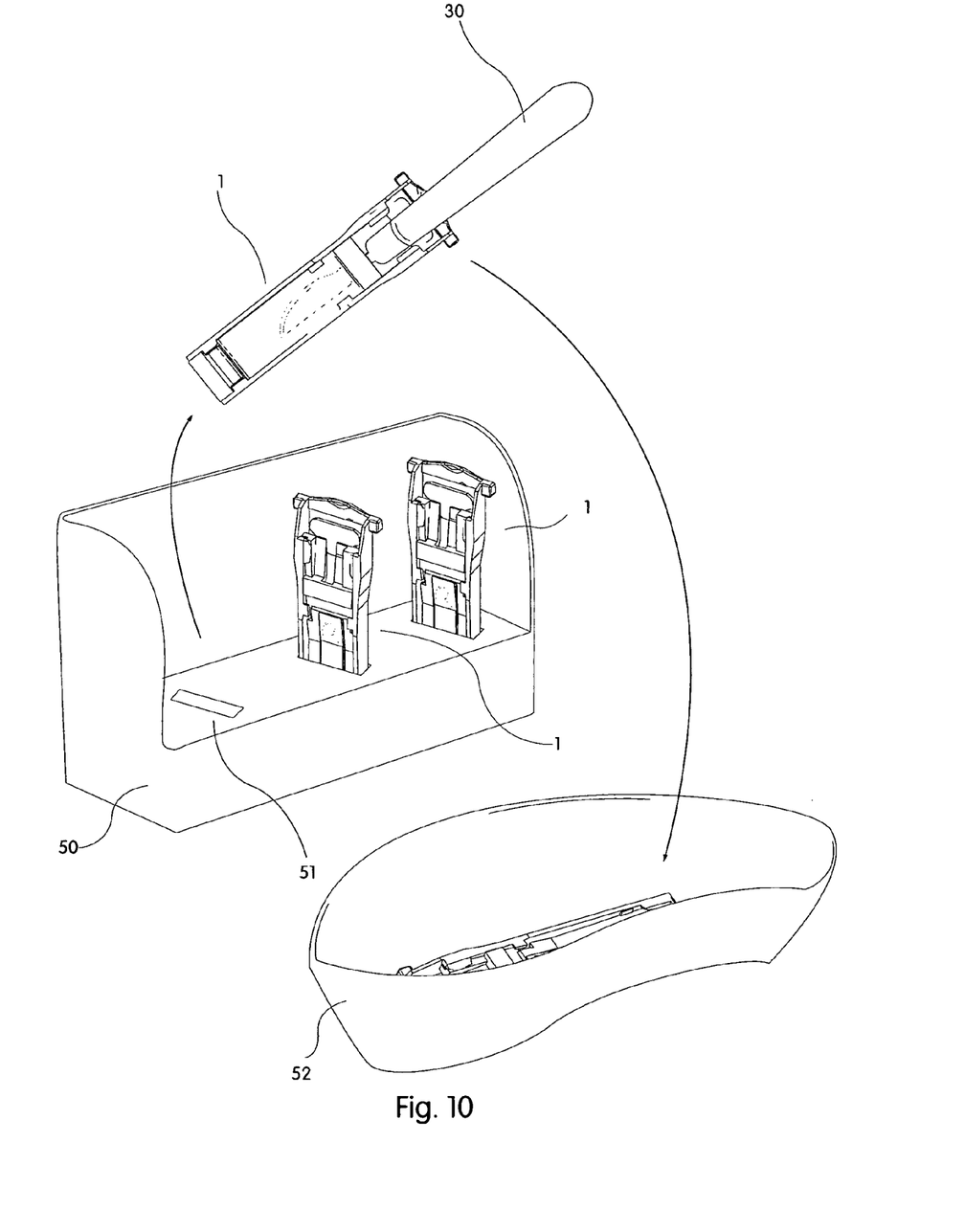
FIG. 10 is a schematic view of a free standing holder for scalpel blade removers of the present invention.

FIG. 10 shows a freestanding base 50 into which scalpel blade removers 1 may be inserted for vertical use. The freestanding base 50 includes slots 51 in which scalpel blade removers 1 are retained. The scalpel blade removers 1 retained in the freestanding base 50 may be used in situ, i.e. with the scalpel 30 inserted whilst the scalpel blade remover 1 is retained in the freestanding base 50. Once the scalpel 30 is inserted such that actuator 3 is in the distal position, the scalpel blade remover 1 and the scalpel 30 may be removed from the freestanding base prior to the scalpel being withdrawn from the scalpel blade remover. The used scalpel blade remover 1 may be disposed of in a kidney dish 52 or any other convenient means.

Figure 11:
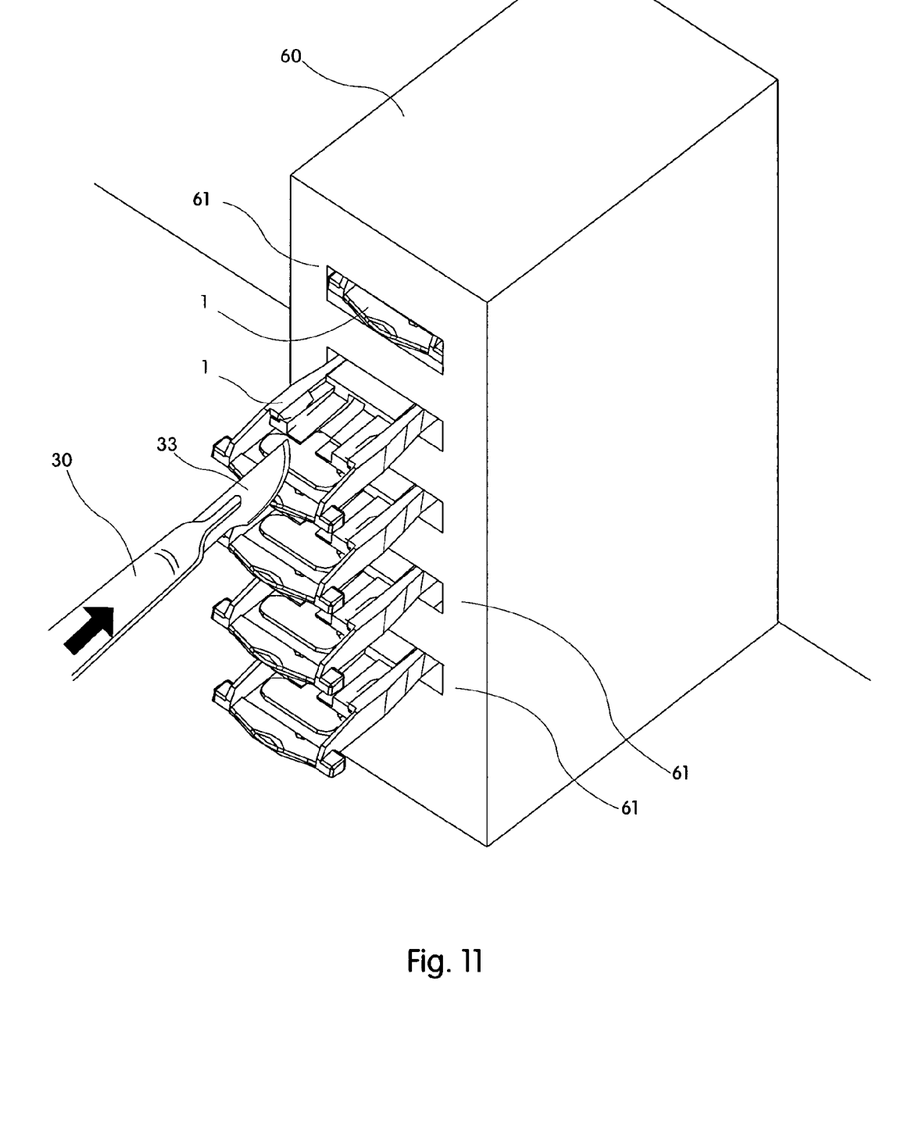
FIG. 11 is a perspective view of a wall mounted holder for scalpel blade removers of the present invention.

FIG. 11 shows a fixed wall-mounted base 60 for horizontal use having a number of slots 61 for retaining scalpel blade removers 1. The mounted base 60 may be used in much the same manner as the freestanding base 50 shown in FIG. 10.

Those skilled in the art will appreciate that the invention is not limited to the exact constructions and operation shown and described above, but includes all suitable modifications and equivalents within the scope of the claims which are to be regarded as including such equivalent constructions insofar as they do not depart from the spirit and concept of the invention. The terms "comprising" and "comprises" as used herein, are to be interpreted in the inclusive sense where the context permits.

The invention claimed is:

1. A scalpel blade remover for removing a blade having a heel from a tang of a scalpel, the remover comprising:
   a housing;
   an actuator having a proximal end, the actuator being operatively juxtaposed with the housing and moveable relative to the housing
   from a proximal position whereat an opening is formed between the actuator and the housing for receiving therebetween the blade on the tang of the scalpel,
   to a distal position;
   a blade deflecting mechanism for automatically separating the heel of the blade from the tang of the scalpel as the actuator is moved to the distal position; and
   a retention mechanism for engaging the actuator and retaining it in the distal position;
   wherein in use, when the blade on the tang is inserted in the opening and the actuator is pushed forward by the tang to its distal position,
   the blade deflecting mechanism automatically separates the heel of the blade from the tang of the scalpel,
   the retention mechanism engages the actuator and retains it in its distal position and limits rearward movement of the blade, and
   upon withdrawal of the tang from the scalpel blade remover, the blade is stripped from the tang and retained between the actuator and the housing.

2. The scalpel blade remover as claimed in claim 1, wherein the retention mechanism is a detent formation on the housing.

3. The scalpel blade remover as claimed in claim 2, wherein the housing has a resiliently flexible arm which is deflected by movement of the actuator to its distal position, and which springs back with an audible click when the actuator reaches its distal position, the detent formation being located on the arm and adapted to engage the proximal end of the actuator to retain it in its distal position.

4. The scalpel blade remover as claimed in claim 2, wherein the detent formation includes two spaced sawtooth detents on either side of the opening.

5. The scalpel blade remover as claimed in claim 1, wherein the blade deflecting mechanism is cam operated.

6. The scalpel blade remover as claimed in claim 5, wherein the blade deflecting mechanism comprises
   at least one cam surface on the housing; and
   at least one cam follower provided on the actuator adjacent its proximal end,
   wherein in use, the cam follower engages with the cam surface as the actuator is moved to the distal position to cause a proximal end portion of the actuator to urge the heel of the blade off the tang.

7. The scalpel blade remover as claimed in claim 6, wherein the proximal end portion of the actuator is bifurcated and has a longitudinal slot for receiving the tang, and a pair of guide surfaces for engagement with the blade on opposite sides of the tang.

8. The scalpel blade remover as claimed in claim 1, wherein the housing and the actuator are integrally formed.

9. The scalpel blade remover as claimed in claim 8, further comprising a bi-fold portion connected between a distal end of the actuator and a distal end of the housing.

10. The scalpel blade remover as claimed in claim 8, wherein the scalpel blade remover is manufactured of thermoplastics material by injection moulding.

11. The scalpel blade remover as claimed in claim 1, wherein the housing is of channel section having opposed sidewalls and a web portion, the actuator being operatively located within the housing in a snap fit and retained therein by tabs on the sidewalls.

12. The scalpel blade remover as claimed in claim 1, in combination with a holder having at least one recess for receiving the scalpel blade remover.

13. The scalpel blade remover as claimed in claim 12 wherein the holder is handheld, the scalpel blade remover being removably and reversibly mountable in the holder.

14. The scalpel blade remover as claimed in claim 12 wherein the holder is fixed, the holder having a plurality of recesses each adapted to receive a scalpel blade remover therein.

15. A scalpel blade remover for removing a blade having a heel from a tang of a scalpel, comprising
   a first member,
   a second member juxtaposed with the first member,
   the first and second members defining a narrow space therebetween for receiving the blade on the tang;
   said second member being engageable by the tang at a first position and moveable relative to the first member by the tang from the first position to a second position,
   a blade deflector for separating the heel of the blade from the tang of the scalpel as the second member is moved to the second position; and
   a mechanism for retaining the second member in the second position;
   wherein in use, when the blade on the tang is inserted in the narrow space and the second member is pushed by the tang from the first position to the second position, the blade deflector disengages the heel of the blade from the tang, the mechanism retains the second member in the second position, and upon withdrawal of the tang, the blade is stripped therefrom.

16. A scalpel blade remover as claimed in claim 15, wherein
   the first member is a housing;
   the second member is an actuator disposed within the housing; and
   the blade deflector is associated with the actuator and is urged into engagement with the heel of the blade to separate the heel of the blade from the tang upon movement of the actuator to the second position.

17. A scalpel blade remover as claimed in claim 16, wherein the mechanism includes a detent.

18. A scalpel blade remover as claimed in claim 17, wherein the detent engages a free proximal end of the actuator to retain the actuator in the second position.

19. A scalpel blade remover as claimed in claim 16, further comprising:
   a camming surface on the housing; and a cam follower provided on the actuator for engagement with the camming surface as the actuator is moved to the distal position to urge the blade deflector into engagement with the heel of the blade.

20. A scalpel blade remover as claimed in claim 16, wherein the blade stripped from the tang is captively retained in the housing.

21. A method of removing a blade from a tang of a scalpel using a scalpel blade remover having a first member, a second member juxtaposed with the first member, the first and second members defining a narrow space therebetween for receiving the blade on the tang, said second member being moveable relative to the first member from the first position to a second position, a blade deflector for separating the heel of the blade from the tang of the scalpel as the second member is moved to the second position, and a mechanism for retaining the second member in the second position;

the method comprising the steps of:

inserting the blade between the first and second members with the blade mounted on the tang of the scalpel;

engaging the second member with the scalpel;

applying a force on the scalpel sufficient to move the second member relative to the first member from the first position to the second position, and to cause the blade deflector to separate a heel of the blade from the tang;

causing the mechanism to retain the second member in the second position; and withdrawing the scalpel to strip the blade from the tang and leave it retained between the first and second members.

22. A method as claimed in claim 21, wherein the first member is a housing;

the second member is an actuator disposed within the housing; and the blade deflector is associated with the actuator and is urged into engagement with the heel of the blade to separate the heel of the blade from the tang upon movement of the actuator to the second position.

23. A method as claimed in claim 22, wherein the step of applying a force includes causing a cam follower on the actuator to move along a camming surface of the housing as the actuator is moved to the second position.

24. A method as claimed in claim 23, wherein the blade deflector is urged by the cam follower into engagement with the heel of the blade to separate the heel from the tang as the actuator moves to its second position, and holds the heel off the tang when the actuator is retained at the second position.

25. A method as claimed in claim 21, wherein the step of causing the mechanism to retain the second member in the second position includes engaging the second member with a detent.

* * * * *